US 11,779,750 B2

(12) United States Patent
Oda et al.

(10) Patent No.: US 11,779,750 B2
(45) Date of Patent: Oct. 10, 2023

(54) NEEDLELESS CONNECTOR WITH VALVE PIVOT SUPPORT

(71) Applicant: CareFusion 303, Inc., San Diego, CA (US)

(72) Inventors: Todd Oda, Torrance, CA (US); Tomas Frausto, Walnut, CA (US); Archana Rao, Los Angeles, CA (US); Ali Saleh, Irvine, CA (US); Siddarth K. Shevgoor, Mission Viejo, CA (US); George Mansour, Diamond Bar, CA (US)

(73) Assignee: CareFusion 303, Inc., San Diego, CA (US)

( * ) Notice: Subject to any disclaimer, the term of this patent is extended or adjusted under 35 U.S.C. 154(b) by 246 days.

(21) Appl. No.: 17/037,442

(22) Filed: Sep. 29, 2020

(65) Prior Publication Data
US 2022/0096816 A1     Mar. 31, 2022

(51) Int. Cl.
*A61M 39/26*  (2006.01)
*F16L 37/413* (2006.01)
*A61M 39/10*  (2006.01)

(52) U.S. Cl.
CPC ............ *A61M 39/26* (2013.01); *A61M 39/10* (2013.01); *F16L 37/413* (2013.01)

(58) Field of Classification Search
CPC .................. A61M 39/10; A61M 39/26; A61M 2039/261; A61M 2039/262; A61M 2039/263; A61M 2039/266; A61M 2039/265; A61M 2039/267; A61M 2039/268; A61M 2039/1072; F16L 29/002; F16L 29/005; F16L 29/02; F16L 29/04;

(Continued)

(56) References Cited

U.S. PATENT DOCUMENTS 2,933,333 A * 4/1960 Bredtschneider ..... F16L 29/005
285/119
3,285,627 A * 11/1966 Kozulla ................ F16K 15/144
285/353

(Continued)

FOREIGN PATENT DOCUMENTS

EP     3124073 A1     2/2017

OTHER PUBLICATIONS

International Search Report and Written Opinion for Application No. PCT/US2021/051820, dated Jan. 25, 2022, 14 pages.

*Primary Examiner* — Kevin F Murphy
*Assistant Examiner* — Jonathan J Waddy
(74) *Attorney, Agent, or Firm* — Morgan, Lewis & Bockius LLP (57) ABSTRACT

A needleless connector includes a housing having a central longitudinal axis, a body portion, and a base portion. The body portion includes an inner surface forming an internal cavity, and a first port forming a first fluid passage to the housing cavity. The base portion includes a top end section and a bottom end section. The top end section has a protrusion, and the bottom end portion has a second port forming a second fluid passage to the housing cavity. The needleless connector further includes a valve having a wall with an inner surface forming a valve cavity. The valve is coupled with the housing such that the protrusion is positioned in the valve cavity, and a proximal end of the protrusion is spaced apart from a proximal end of the valve cavity.

20 Claims, 5 Drawing Sheets

(58) Field of Classification Search
CPC . F16L 37/28; F16L 37/30; F16L 37/32; F16L 37/34; F16L 37/35; F16L 37/38; F16L 37/40; F16L 37/413; F16L 37/42
USPC .......................................................... 604/256
See application file for complete search history.

(56) References Cited

U.S. PATENT DOCUMENTS

| | | | | |
|---|---|---|---|---|
| 3,986,508 | A * | 10/1976 | Barrington | A61M 39/14 |
| | | | | 604/905 |
| 4,019,512 | A * | 4/1977 | Tenczar | A61M 39/14 |
| | | | | 604/905 |
| 5,730,418 | A * | 3/1998 | Feith | A61M 39/26 |
| | | | | 604/905 |
| 5,782,816 | A | 7/1998 | Werschmidt et al. | |
| 2004/0084095 | A1* | 5/2004 | Knowles | F16L 37/30 |
| | | | | 137/614 |
| 2005/0010177 | A1* | 1/2005 | Tsai | A61M 39/26 |
| | | | | 604/256 |
| 2005/0087715 | A1* | 4/2005 | Doyle | A61M 39/26 |
| | | | | 604/537 |
| 2012/0059334 | A1 | 3/2012 | Pan | |
| 2016/0038701 | A1* | 2/2016 | White | A61M 39/26 |
| | | | | 251/61.1 |
| 2017/0072182 | A1* | 3/2017 | Tsai | A61M 39/26 |
| 2017/0189665 | A1* | 7/2017 | Ueda | A61M 39/24 |

* cited by examiner

NEEDLELESS CONNECTOR WITH VALVE PIVOT SUPPORT

TECHNICAL FIELD

The present disclosure relates generally to needleless connectors, and, in particular, to needleless connectors with a valve member having a protrusion that allows the valve to tilt and pivot away from the face of the syringe face as the valve is pushed down by the syringe, thereby allowing fluid to flow between the syringe and a housing cavity of the needleless connector.

BACKGROUND

Medical treatments often include the infusion of a medical fluid (e.g., a saline solution or a liquid medication) to patients using an intravenous (IV) catheter that is connected though an arrangement of flexible tubing and fittings, commonly referred to as an "IV set," to a source of fluid, for example, an IV bag. Certain needleless connectors may be used in an IV set and may have a self-sealing port to prevent leakage of fluid when a mating medical implement is decoupled from such a needleless connector. Additionally, a needleless connector may include a mechanical valve, for example, a collapsible valve comprising a flexible material for providing the self-sealing port and controlling the flow of fluid within the IV set.

Due to the nature of currently existing and/or prior art needleless valve geometries, fluid is commonly deposited on the face of the valve head upon removal of a medical implement (e.g., a mating male luer or a syringe) used to apply an axial force to place the valve member in an open position. In these currently existing needleless valves, fluid deposited on the valve head will occasionally separate from the valve member and flow into the fluid path for administering to a patient, thereby causing anxiety along with potential blood stream diseases.

The description provided in the background section should not be assumed to be prior art merely because it is mentioned in or associated with the background section. The background section may include information that describes one or more aspects of the subject technology.

SUMMARY

According to various aspects of the present disclosure, a needleless connector may include a housing having a central longitudinal axis, a body portion, and a base portion. The body portion may include an inner surface forming an internal cavity, and a first port forming a first fluid passage to the internal cavity. The base portion may include a top end section and a bottom end section. The top end section may include a protrusion, and the bottom end section may include a second port forming a second fluid passage to the internal cavity. The needleless connector may further include a valve with a wall having an inner surface forming a valve cavity. The valve may be coupled with the housing such that the protrusion is positioned in the valve cavity, and a proximal end of the protrusion is spaced apart from a proximal end of the valve cavity.

According to various aspects of the present disclosure, a needleless connector may include a housing having a central longitudinal axis, a body portion, and a base portion. The body portion may include an inner surface forming a housing cavity, and a first port forming a first fluid passage to the housing cavity. The base portion may include a top end section and a bottom end section. The top end section may include a protrusion, and the bottom end section may include a second port. The needleless connector may further include a valve having a first end portion, a second end portion, and an inner surface forming a valve cavity. The valve may have a closed configuration in which the first fluid passage is obstructed by the second end portion of the valve, and an open configuration in which the valve is compressed toward the base portion such that the first fluid passage is unobstructed. When the valve moves from the closed configuration toward the open configuration, the first end portion of the valve may engage against the protrusion such that the second end portion of the valve moves in a direction that is transverse relative to the central longitudinal axis.

It is to be understood that both the foregoing general description and the following detailed description are exemplary and explanatory and are intended to provide further explanation of the subject technology as claimed. It is also to be understood that other aspects may be utilized, and changes may be made without departing from the scope of the subject technology.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

Various embodiments of the present disclosure are generally directed to a self-sealing, needleless connector that incorporates a resilient, compressible valve disposed within a housing of the connector, in which the compressible valve has a housing including a base including a protrusion extending towards the inlet port of the housing. The protrusion obstructs the valve from travelling down on one side and allows the valve to pivot down and away from the face of a syringe inserted into the needleless connector as the valve is pushed further down, allowing fluid flow from the syringe into the cavity of the housing.

In some embodiments, the valve may be designed with two different spring rates, a higher spring rate for the primary seal area and a lower spring rate for the secondary seal area. The housing may further include fluid channels positioned on an inner surface of the housing at a position between an internal sealing edge of the housing and the top surface of the inlet port. In conjunction with the flow channels, the two different spring rates help prevent droplet formation. In particular, to prevent droplet formation upon disconnection, as the syringe is pulled from the connector, the primary seal is the first to seal due to the higher spring rate. As the syringe continues to be removed, the secondary seal of the valve travels upwards, creating a vacuum between the primary and secondary seals. The vacuum advantageously pulls any remaining fluid at the tip of the syringe or on the top surface of the valve through the fluid channels. This helps to prevent droplet formation when the syringe is disconnected from the needleless connector. Further advantageously in order to prevent fluid entrapment and to improve flushability, the valve is designed to collapse like a bellows in multiple areas including but not limited to at least one of the head portion and the body portion of the valve. Accordingly, in some embodiments, at least one of the head portion or the body portion of the compressible valve may include a dimple or notch positioned on an outer surface thereof.

As the housing and the valve of the needleless connector of the various embodiments described herein minimizes the amount of fluid capable of being deposited on the valve face, it advantageously prevents anxiety along with potential blood stream diseases commonly associated with fluids deposited on the valve face (top surface) of the valve head.

While the following description is directed to the administration of medical fluid to a patient by a medical practitioner using the disclosed needleless connector, it is to be understood that this description is only an example of usage and does not limit the scope of the claims.

Figure 1A:
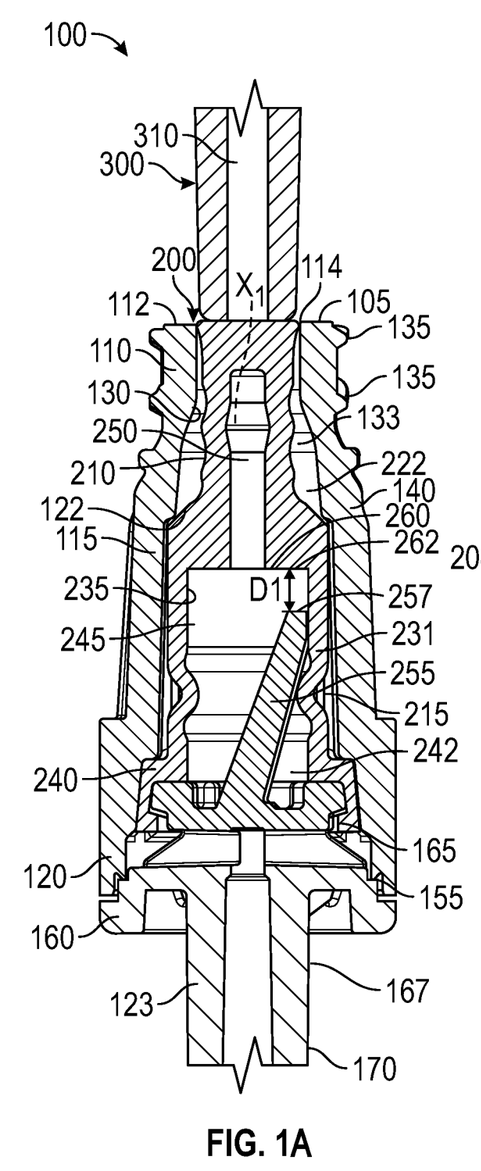
FIG. 1A is a cross-sectional view of a housing of a needleless connector having a compressible valve installed therein, in accordance with some embodiments of the present disclosure.

FIG. 1A is a cross-sectional view of a housing 110 of a needleless connector 100 having a compressible valve 200 installed therein, in accordance with some embodiments of the present disclosure. As depicted, the housing 110 may have a proximal end 105 defining an inlet port 112 of the housing 110, a distal end 120 including a base portion 160 defining an outlet port 123 of the housing 110, and a central longitudinal axis $X_1$ extending through the proximal and distal ends 105 and 120, In some embodiments, the housing 110 may further include an inner surface 130 defining an internal cavity 133 which extends at least partially between the proximal and distal ends 105 and 120 of the housing 110. The housing 110 may be formed of a body portion 115 coupled to or otherwise integrally formed with the base portion 160. However, in some embodiments, the housing 110 may be formed from a combination of other pieces or parts similarly dimensioned to house the compressible valve 200 therein. In operation, a fluid pathway may be established through needleless connector 100 from the inlet port 112 to the outlet port 123, for example. As referred to herein, proximal refers to an orientation toward the inlet port 112 of the housing 110, and distal refers to an orientation toward the base portion 160 or bottom of the housing 100, opposite the inlet port 112.

As depicted, in addition to housing 110 including the inlet port 112 of the housing 110 for interfacing with a medical implement 300, the housing 110 may further include an opening 155 for connecting with the base portion 160 of the housing 110. The lower section of the body portion 115 (e.g., a section proximal to the opening 155) may have an increased diameter and include one or more internal contact tabs (not shown). When assembled in a needleless connector 100, the one or more internal contact tabs may provide a radial force substantially orthogonal to the central longitudinal axis $X_1$ of the housing 110 onto a flange portion of the compressible valve 200 that is arranged on a valve mount of the base portion 160.

In accordance with various embodiments of the present disclosure, the inlet port 112 may include a top port surface 114 and a channel defined in the internal cavity 133. The inlet port 112 may include engagement features 135 for coupling to another device (e.g., a fluid transfer assembly). For example, engagement features 135 may include cooperating mechanical elements, such as internal or external surface threads, detents, bayonet-type locking elements, etc., as well as other surface configurations, such as a tapered Luer surface for frictional engagement. In some embodiments, the inlet port 112 may define a female luer fitting with luer lock threading 135. The inner surface 130 and the internal cavity 133 defined therein may extend longitudinally from the opening of the top port surface 114 of the inlet port 112 into the body portion 115 of the housing 110.

In some embodiments, an internal sealing edge 122 may be defined on the inner surface 130 of the housing 110. The internal sealing edge 122 may be a circumferential edge and configured for retaining the compressible valve 200 within the internal cavity 133 of the assembled needleless connector 100. In operation, the internal sealing edge 122 may be arranged to provide blocking of fluid flow in conjunction with a primary seal portion 225 (illustrated in FIG. 2) of the compressible valve 200.

According to various aspects of the present disclosure, the base portion 160 may have a top end section 165 and a bottom end section 167 located distally to the top end section 165. As depicted, a protrusion 255 may be disposed on and extend proximally from the top end section 165. The protrusion 255 may be in the form of a longitudinal body, which extends angularly from a central portion of the base top end section 165 towards the proximal end 105 of the housing 110. As shall be described in further detail below, with reference to FIG. 2 and continued reference to FIG. 1A, the protrusion may function as a valve pivot to tilt a head portion 220 of the valve 200 when the valve member is subject to an axial force F during syringe 300 insertion. In some embodiments, the bottom end section 167 may define the outlet port 123, which forms a second fluid passage 170 to the internal cavity 133.

Figure 1B:
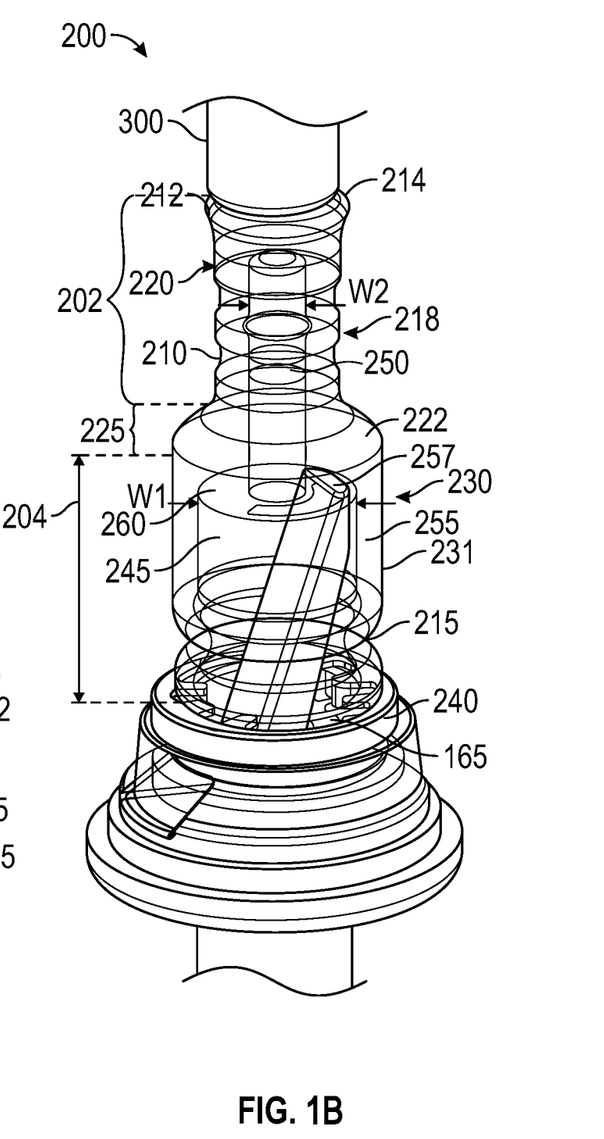
FIG. 1B is a perspective view illustrating an example of a compressible valve of a needleless connector, in accordance with some embodiments of the present disclosure.

FIG. 1B is a perspective view illustrating an example of a compressible valve 200 of a needleless connector 100, in accordance with some embodiments of the present disclosure. As depicted, compressible valve 200 may include head portion 220, and body portion 230 extending distally from the head portion 220. In certain embodiments, the head portion 220 includes a compressible column section 218 and may define an axial center $X_2$ of the compressible valve 200 in a non-activated state (before an applied axial force F causes the head portion 220 to tilt, as illustrated in FIG. 3C). The axial center $X_2$ may substantially correspond to the central longitudinal axis $X_1$ of the needleless connector housing 110 when assembled therein in a closed state of the compressible valve 200. In the non-activated state (e.g., in isolation or within a connector but not displaced by a medical implement) the axial center $X_2$ may extend longitudinally through the head portion 220 and the body portion 230 of the compressible valve 200 (as depicted in FIG. 1A). In the aforementioned state, the body portion 230 of the compressible valve 200 may have the same axial center as the head portion 220 or other portions of the compressible valve 200. However, as described in further detail below, in an activated state (e.g., when the axial force F is applied to the compressible valve 200 using the medical implement or syringe 300) the axial center $X_2$ of the compressible valve 200 may change and pivot in relation to the central longitudinal axis $X_1$ upon the compressible valve 200 being activated by the medical implement or syringe 300.

In accordance with some embodiments, the head portion 220 may include a top section 212 defining a secondary seal portion 214 of the compressible valve 200. The body portion 230 may further define a second or primary seal portion 225 at a proximal end of the body portion 230. As depicted, the primary seal portion 225 may be disposed distally to the secondary seal portion 214.

According to various aspects of the present disclosure, the valve 200 may have a wall 231 including an inner surface 235 that defines a valve cavity 242. As depicted, the valve 200 may be coupled with the housing 110 such that the protrusion 255 is positioned in the valve cavity 242. The protrusion 255 and the valve cavity 242 may each have a distal end. The proximal end 257 of the protrusion 255 may be spaced apart from the proximal end 262 of the valve cavity 242. In particular, in the non-activated or closed state of the valve 200, a distance or space D1 may be defined between the proximal end 257 of the protrusion 255 and the proximal end 262 of the valve cavity 242.

In some embodiments, the valve 200 may further include a first end portion 202 and a second end portion 204 extending distally to the first end portion 202. For example, the first end portion may define a secondary portion 202 of the valve 200 and the second end portion may define a primary portion 204 of the valve. Additionally, in some embodiments the valve cavity 242 may extend proximally through the primary portion 204 of the valve and enter the secondary portion 202 of the valve. Accordingly, the valve cavity 242 may include a first valve cavity 245 and a second valve cavity 250 fluidly communicated with the first valve cavity. As depicted, the first valve cavity 245 may extend through the first end portion (secondary portion) 202 of the valve 200 toward the second end portion (primary portion) 204 of the valve 200. The second valve cavity 250 may extend from the first valve cavity 245 into the second end portion (primary portion) 204 of the valve 200. In the assembled state of the housing 110 and the valve 200, the proximal end 257 of the protrusion may be positioned in the first valve cavity 245 longitudinally spaced apart from the second valve cavity 250 by the distance D1.

The first valve cavity 245 may have a first cross-sectional width W1 and the second valve cavity 250 may have a second cross-sectional width W2. In some embodiments, the second cross-sectional width W2 may be less than the first cross-sectional width W1. The aforementioned configuration is advantageous as shall be described in further detail below in that it allows for compressing or collapsing of the primary portion 204 before compressing or collapsing of the secondary portion 202 of the valve 200 until the point where protrusion (also referred to as a valve pivot support) contacts the inner surface 235 of the valve 200. Accordingly, less axial force F may be required to displace the valve 200 of the various embodiments described herein to an open position, as compared with currently existing needleless valves. Due to the difference in cross-sectional widths of first and second valve cavities 245 and 250, a ridge 260 may be defined between the first and second valve cavities. As depicted, in the closed or non-activated state, the proximal end 257 of the protrusion 255 may be longitudinally aligned and spaced apart from the ridge 260 by the distance D. As shall be described in further detail below, as the secondary portion 202 of the valve is activated by the axial force F and the primary portion 204 compresses or collapses distally towards the base portion 160, the ridge 260 engages against the proximal end 257 of the protrusion 255. Accordingly, the secondary portion 202 of the valve may be translated distally within the internal cavity 133. When the second end portion (primary portion) 204 of the valve collapses, the valve 200 may engage against the protrusion 255 such that the first end portion (secondary portion) 202 of the valve may move in a direction that is transverse relative to the longitudinal axis X1 of the housing 110.

In some embodiments of the present disclosure, a wall 231 of the valve 200 may be more flexible along the first end portion (secondary portion) 202 of the valve 200 than along the second end portion (primary portion) 204. For example, the wall 231 of the valve 200 may have a lower spring rate along the first end portion (secondary portion) 202 of the valve 200 than along the second end portion (primary portion) 204. The aforementioned configuration may be achieved in part due to the differing cross-sectional widths W1 and W2 of the respective valve cavities 250 and 245 defined in the respective secondary and primary valve portions 202 and 204.

According to various aspects of the present disclosure, the wall 231 of the valve 200 may include a first and second dimples or notches 210 and 215 and the proximal end 257 of the protrusion 255 may be positioned between the first and second dimples 210 and 215 and the proximal end 262 of the valve cavity 242. The aforementioned configuration is advantageous in further reducing the spring rate of the second end portion (primary portion) 204 of the valve 200. It is to be understood that while the notches 210 and 215 are shown generally opposite each other on the wall 231 of the body portion 230, other arrangements of the at least one notch 210 on the column section 218, including three or more notches, are contemplated. For example, the dimples 210 and 215 may be disposed on opposite sides of the interior wall 231 and at longitudinally different positions. Moreover, the size and shape of each interior dimple 210 and 215 may be distinct. In certain embodiments, the first interior dimple 210 may be larger than the second interior dimple 215.

Figure 2:
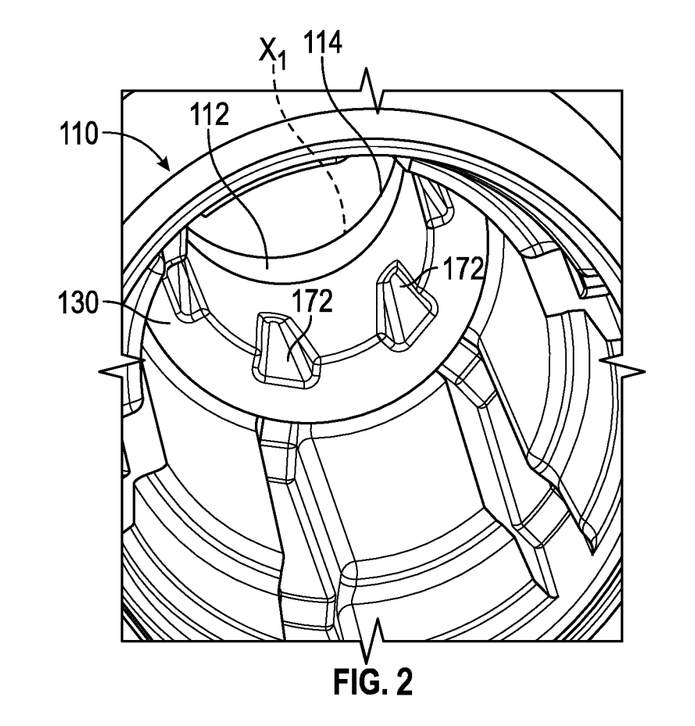
FIG. 2 is a perspective view of an inner surface of the housing of the needleless connector of FIG. 1, in accordance with some embodiments of the present disclosure.

FIG. 2 is a perspective view of an inner surface 130 of the housing 110 of the needleless connector 100 of FIG. 1, in accordance with some embodiments of the present disclosure. In some embodiments, the housing 110 may further include a plurality of fluid channels 172 positioned on the inner surface 130 at a position between the internal sealing edge 122 and the top surface 114 of the inlet port 112. In particular, the fluid channels 172 may be positioned above the internal sealing edge 122 and below the top surface 114 of the inlet port 112. The aforementioned configuration is advantageous because in operation, the fluid channels 172 draw fluid away from the top section 212, which defines the secondary seal portion 214 of the valve 200 and from the syringe face 312 to prevent droplet formation once the syringe 300 is completely separated from the needleless valve connector 100.

According to various embodiments of the present disclosure, the compressible valve 200 may include any of the various materials used for producing mechanical valves for needleless connectors and other medical implements. In some implementations, the head portion 220 may include an elastomeric material, such as but not limited to, a silicone compound. Moreover, the primary seal portion 225 and lower portion 230 may include an elastomeric material. In some embodiments, all or some of the flexible valve may be formed of liquid silicone rubbers.

In accordance with some embodiments, and referring again to FIG. 1A, the primary seal portion 225 may have a cross-sectional area greater than a cross-sectional area of the column section 218 of the head portion 220. For example, the primary seal portion 225 may be in the form of a frustoconical surface 222 for engaging with the internal sealing edge 122 of the connector housing 110. The frustoconical shape of the primary seal portion 225 may be configured such that a first cross-sectional area of the primary seal portion 225 proximal the head portion 220 is smaller than a second cross-sectional area of the primary seal portion 225 distal to the head portion 220. In other words, the primary seal portion 225 may be narrower towards the head portion 220 and wider towards the lower portion 230.

In some embodiments, the lower portion 230 may be in the form of an elongated tubular member 231 having a closed end proximal the primary seal portion 225 and an open end distal the primary seal portion 225. As such, an interior air space may be defined in the interior of the compressible valve 200. According to some aspects, the compressible valve 200 may be collapsible in operation with a needleless connector assembly. In these embodiments, the lower portion 230 may include the dimples 210 and 215 and/or incisions to facilitate proper collapsing functionality in accordance with different embodiments of the present disclosure. Moreover, while the head portion 220 of the compressible valve 200 may have generally cylindrical properties allowing it to operate with a male luer-tapered tip of a medical implement or similar interconnection device, the lower portion 230 may be in the form of a plurality of shapes, sizes, and characteristics associated with the functionality and operation of the compressible valve in conjunction with the needleless connector apparatus in which it is used. In some embodiments, when the lower portion 230 has a tubular section 231, this section 231 may comprise a plurality tubular shapes, such as, but not limited to, cylindrical, rectangular, hexagonal, tubular shapes.

Figure 3A:
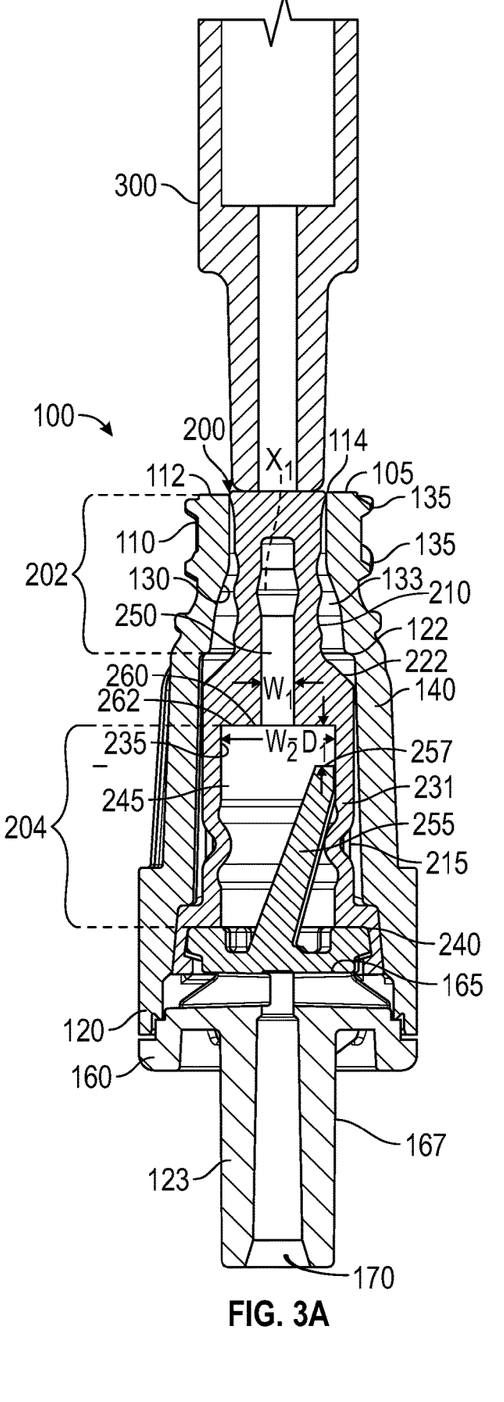
FIG. 3A is a cross-sectional view of the assembled needleless connector housing and compressible valve of FIG. 1A in a closed position, in accordance with some embodiments of the present disclosure.

FIG. 3A is a partial cross-sectional view of the assembled needleless connector 100 with housing 110 and compressible valve 200 of FIG. 1 in a closed position before insertion of a medical implement, in accordance with some embodiments of the present disclosure. Referring to FIG. 3A with continued reference to FIG. 1, the assembled needleless connector 100 as illustrated in FIG. 3A is in a sealed configuration such that any fluid from an interconnected fluid path coupled to the outlet port 123 is sealed from the inlet port 112. In some embodiments, the needleless connector 100 may be assembled such that the flange portion 240 of the compressible valve 200 is coupled, snapped, or otherwise attached onto a valve mount of the base portion 160.

The internal cavity 133 of the housing 110 may be arranged on top of the compressible valve 200 coupled to the base portion 160 such that the head portion 220 of the compressible valve 200 is aligned and disposed within the inlet port 112. Upon assembly, the top surface 216 of the head portion 220 of the compressible valve 200 may have a resulting plane that is substantially perpendicular to the central longitudinal axis $X_2$ or axial center of the column section 218 of the head portion 220 when the head portion 220 is engaged within the inlet port 112 of the housing 110. Additionally, the one or more internal contact tabs (not shown) disposed on the lower section of the body portion 115 of the housing 110 may surround and apply pressure to a sidewall of the flange portion 240 to secure and/or anchor the compressible valve 200 in the housing 110. In operation, the compressible valve 200 of the needleless connector can compress, collapse, cant and/or fold when the axial force F (illustrated in FIG. 3B) is applied to the top surface 216 of the compressible valve 200 and expand and realign when the axial force F is removed, as shall be described in further detail below.

Accordingly, the one or more internal contact tabs (not shown) may provide a radial force substantially orthogonal to the central longitudinal axis $X_2$ onto the sidewall of the flange portion 240. In this regard, when the axial force F is applied to the top surface 216 of the head portion 220 of the compressible valve 200, the effect of any resulting axial force through the compressible valve 200 onto the base portion 120 of the housing 100 is reduced if not eliminated. Such a resulting axial force applied onto the base portion 120 can work against or in derogation, for example, to a fused connection between the base portion 120 and the body portion 115, and over time may disadvantageously cause the fused connection to become breached and/or separated.

Figure 3B:
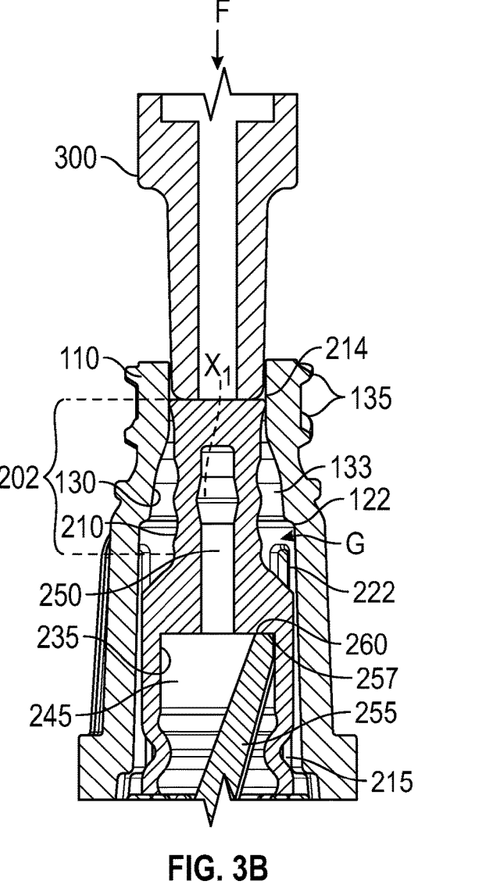
FIG. 3B is a cross-sectional view of the assembled needleless connector housing and compressible valve of FIG. 1A during initial syringe insertion, in accordance with some embodiments of the present disclosure.
Figure 3C:
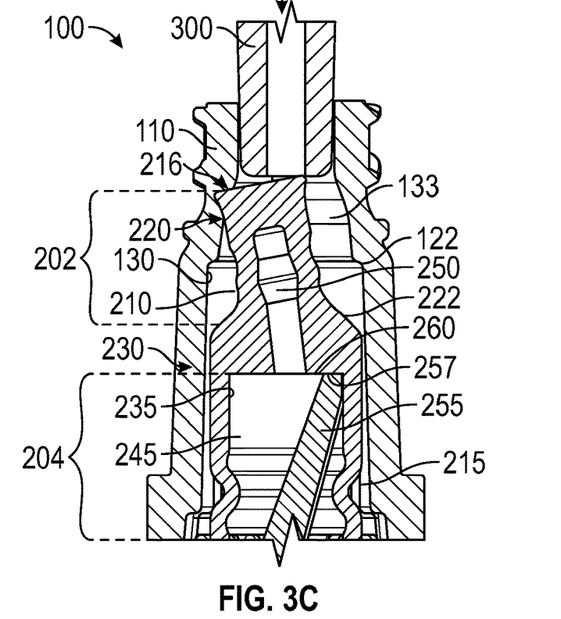
FIG. 3C is a cross-sectional view of the assembled needleless connector housing and compressible valve of FIG. 1A during further syringe insertion, in accordance with some embodiments of the present disclosure.

FIG. 3B is a cross-sectional view of the assembled needleless connector housing and compressible valve of FIG. 1A during initial syringe insertion, in accordance with some embodiments of the present disclosure. As the medical implement 300 (e.g., a syringe) is initially inserted into the inlet port 112 of the needleless connector 100, an axial force F is exerted onto the compressible valve 200 such that the compressible valve is displaced distally causing the frustoconical surface 222 of the primary seal portion 225 to separate from the internal sealing edge 122. As briefly described above because the second cross-sectional width W2 may be less than the first cross-sectional width W1, the primary portion 204 of the valve 200 collapses or compresses before the secondary portion 202 of the valve 200 compresses or collapses. This occurs until the point where the protrusion 255 (also referred to as a valve pivot support) contacts the inner surface 235 of the valve 200. As the secondary portion 202 of the valve is activated by the axial force F and the primary portion 204 compresses or collapses distally towards the base portion 160, the ridge 260 engages against the proximal end 257 of the protrusion 255. Accordingly, the secondary portion 202 of the valve may be translated distally within the internal cavity 133. When the first end portion (secondary portion) 202 of the valve collapses, the valve 200 may engage against the protrusion 255 such that the first end portion (secondary portion) 202 of the valve may move in a direction that is transverse relative to the longitudinal axis X1 of the housing 110.

FIG. 3C is a cross-sectional view of the assembled needleless connector housing and compressible valve of FIG. 1A during further syringe insertion, in accordance with some embodiments of the present disclosure. As the axial force F continues to be applied, the medical implement 300 may descend further into the inlet port 112 to allow fluid flow from the syringe 300 into the cavity 133. The secondary portion 202 of valve 200 may further compress, collapse, and tilt. As the secondary portion 202 folds or collapses, the top surface 216 may tilt downwardly (distally, as illustrated in FIG. 3C) due to presence of the protrusion 255 (valve pivot support).

Figure 4A:
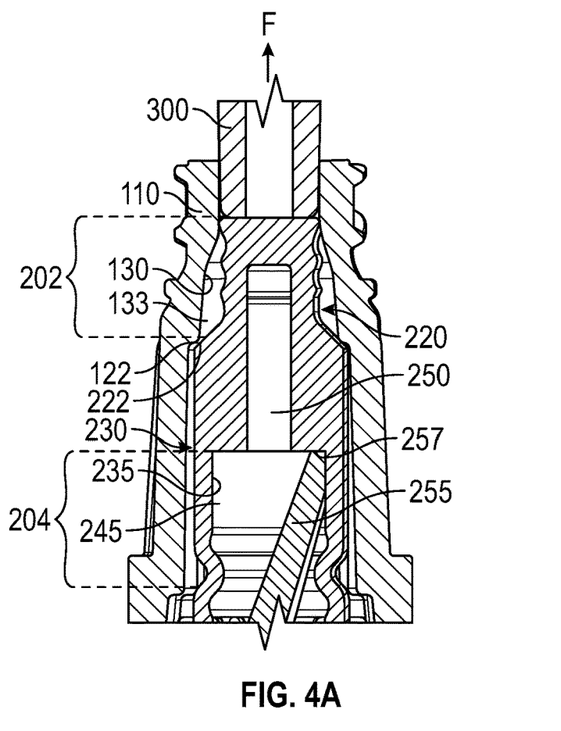
FIG. 4A is a cross-sectional view of the assembled needleless connector housing and compressible valve of FIG. 1A during initial syringe removal, in accordance with some embodiments of the present disclosure.
Figure 4B:
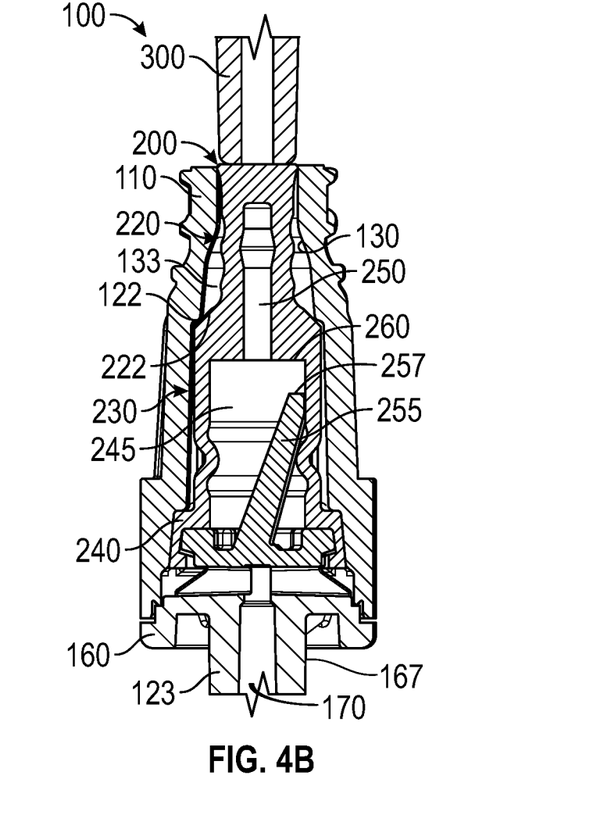
FIG. 4B is a cross-sectional view of the assembled needleless connector housing and compressible valve of FIG. 1A completing syringe removal, in accordance with some embodiments of the present disclosure.

FIG. 4A is a cross-sectional view of the assembled needleless connector housing and compressible valve of FIG. 1A during initial syringe removal, in accordance with some embodiments of the present disclosure. As the syringe 300 is removed from the inlet port 212, the compressible valve 200 may begin to expand to return to its position within the housing in the sealed configuration as illustrated in FIG. 3. In particular, as discussed above, since the wall 231 of the valve 200 may have a lower spring rate along the first end portion (secondary portion) 202 of the valve 200 than along the second end portion (primary portion) 204, the primary portion 204 of the valve 200 travels faster allowing the primary seal portion 225 of the valve 200 to first contact the internal sealing edge 122. As the compressible valve 200 expands further, the secondary portion 202 of valve continues to move proximally, creating a vacuum between the secondary seal portion 214 and the primary seal portion 225 of the compressible valve 200. Due to the vacuum, any remaining fluid at the tip of the syringe 300 or on the top surface 216 of the valve is pulled through the fluid channels 172 on the inner surface 130 of the housing 110. Accordingly, droplet formulation on the top surface of the valve 216 may be prevented when the syringe 300 is disconnected from the connector 100.

Various examples of aspects of the disclosure are described as numbered clauses (1, 2, 3, etc.) for convenience. These are provided as examples and do not limit the subject technology. Identification of the figures and reference numbers are provided below merely as examples for illustrative purposes, and the clauses are not limited by those identifications.

Clause 1: A needleless connector comprising: a housing comprising a central longitudinal axis, a body portion, and a base portion, the body portion comprising an inner surface forming an internal cavity, and a first port forming a first fluid passage to the internal cavity, the base portion comprising a top end section and a bottom end section, the top end section comprising a protrusion, and the bottom end section comprising a second port forming a second fluid passage to the internal cavity; and a valve comprising a wall having an inner surface forming a valve cavity, wherein the valve is coupled with the housing such that the protrusion is positioned in the valve cavity, and a proximal end of the protrusion is spaced apart from a proximal end of the valve cavity.

Clause 2: The needleless connector of Clause 1, wherein the internal cavity is formed between the first and second ports.

Clause 3: The needleless connector of Clause 1, wherein the proximal end of the protrusion is positioned between the central longitudinal axis and the inner surface of the valve.

Clause 4: The needleless connector of Clause 1, wherein the valve comprises a first end portion and a second end portion, and the valve cavity comprises a first valve cavity and a second valve cavity, the first valve cavity extending through the first end portion of the valve toward the second end portion of the valve, and the second valve cavity extending from the first valve cavity into the second end portion of the valve.

Clause 5: The needleless connector of Clause 4, wherein the proximal end of the protrusion is positioned in the first valve cavity.

Clause 6: The needleless connector of Clause 4, wherein the wall of the valve along the first end portion has a lower spring rate than the wall of the valve along the second end portion.

Clause 7: The needleless connector of Clause 4, wherein the valve comprises a ridge between the first valve cavity and the second valve cavity, and the proximal end of the protrusion is longitudinally aligned with the ridge.

Clause 8: The needleless connector of Clause 7, wherein, when the valve is compressed toward the base portion, the ridge engages against the protrusion.

Clause 9: The needleless connector of Clause 4, wherein the first valve cavity comprises a first cross-sectional width and the second valve cavity comprises a second cross-sectional width, wherein the second cross-sectional width is less than the first cross-sectional width such that a ridge is formed between the first and second valve cavities.

Clause 10: The needleless connector of Clause 4, wherein, when the valve is compressed toward the base portion, the first end portion of the valve collapses before the second end portion of the valve.

Clause 11: The needleless connector of Clause 4, wherein, when the first end portion of the valve collapses, the valve engages against the protrusion such that the second end portion of the valve moves in a direction that is transverse relative to the central longitudinal axis.

Clause 12: The needleless connector of Clause 1, wherein the wall of the valve comprises first and second dimples, and wherein the proximal end of the protrusion is between the first and second dimples and a proximal end of the valve cavity.

Clause 13: The needleless connector of Clause 1, wherein an outer surface of the valve comprises a primary seal portion and a secondary seal portion, and wherein the primary seal portion is spaced apart from the secondary seal portion.

Clause 14: The needleless connector of Clause 13, wherein the primary seal portion is configured to engage against the inner surface of the body portion to form a primary seal therebetween, and the secondary seal portion is configured to engage against the inner surface of the body portion to form a secondary seal therebetween.

Clause 15: The needleless connector of Clause 14, wherein the inner surface of the body portion comprises a sealing edge between the first port and the base portion.

Clause 16: The needleless connector of Clause 15, wherein the inner surface of the body portion comprises a fluid channel extending between the first port and the sealing edge.

Clause 17: A needleless connector comprising: a housing comprising a central longitudinal axis, a body portion, and a base portion, the body portion comprising an inner surface forming a housing cavity, and a first port forming a first fluid passage to the housing cavity, the base portion comprising a top end section and a bottom end section, the top end section comprising a protrusion, and the bottom end section comprising a second port; and a valve comprising a first end portion, a second end portion, and an inner surface forming a valve cavity, the valve having a closed configuration in which the first fluid passage is obstructed by the second end portion of the valve, and an open configuration in which the valve is compressed toward the base portion such that the first fluid passage is unobstructed, wherein, when the valve moves from the closed configuration toward the open configuration, the first end portion of the valve engages against the protrusion such that the second end portion of the valve moves in a direction that is transverse relative to the central longitudinal axis.

Clause 18: The needleless connector of Clause 17, wherein, when the valve moves from the closed configuration toward the open configuration, an inner surface of the valve engages against a distal end of the protrusion.

Clause 19: The needleless connector of Clause 17, wherein, when the valve moves from the closed configuration toward the open configuration, the second end portion begins to collapse after the first end portion begins to collapse.

Clause 20: The needleless connector of Clause 17, wherein an outer surface of the valve comprises a primary seal portion and a secondary seal portion, and wherein, when the valve moves from the open configuration toward the closed configuration, the second end portion longitudinally expands such that the secondary seal portion and the primary seal portion move away from each other to form a vacuum between an outer surface of the valve and the inner surface of the body portion.

Clause 21: The needleless connector of Clause 20, wherein the inner surface of the body portion comprises a fluid channel configured to permit a fluid to move between the secondary seal portion and the inner surface of the housing into an area between the secondary seal portion and the primary seal portion.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, or operations in the processes or methods disclosed are illustrations of exemplary approaches. Based upon implementation preferences or scenarios, it is understood that the specific order or hierarchy of steps, operations or processes may be rearranged. Some of the steps, operations or processes may be performed simultaneously. In some implementation preferences or scenarios, certain operations may or may not be performed. Some or all of the steps, operations, or processes may be performed automatically, without the intervention of a user. The accompanying method claims present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A needleless connector comprising:
a housing comprising a central longitudinal axis, a body portion, and a base portion, the body portion comprising an inner surface forming an internal cavity, and a first port forming a first fluid passage to the internal cavity, the base portion comprising a top end section, a bottom end section, and a protrusion, and the bottom end section comprising a second port forming a second fluid passage to the internal cavity, wherein the protrusion extends from a central portion of the top end section in a direction away from the central longitudinal axis; and
a valve comprising a wall having an inner surface forming a valve cavity, wherein the valve is coupled with the housing such that the protrusion is positioned in the valve cavity, and a proximal end of the protrusion is spaced apart from a proximal end of the valve cavity.

2. The needleless connector of claim 1, wherein the internal cavity is formed between the first and second ports.

3. The needleless connector of claim 1, wherein the valve comprises a first end portion and a second end portion, and the valve cavity comprises a first valve cavity and a second valve cavity, the first valve cavity extending through the second end portion of the valve toward the first end portion of the valve, and the second valve cavity extending from the first valve cavity into the first end portion of the valve.

4. The needleless connector of claim 3, wherein the proximal end of the protrusion is positioned in the first valve cavity.

5. The needleless connector of claim 3, wherein the wall of the valve along the second end portion has a lower spring rate than the wall of the valve along the first end portion.

6. The needleless connector of claim 3, wherein the valve comprises a ridge between the first valve cavity and the second valve cavity, and the proximal end of the protrusion is longitudinally aligned with the ridge.

7. The needleless connector of claim 6, wherein, when the valve is compressed toward the base portion, the ridge engages against the protrusion.

8. The needleless connector of claim 3, wherein the first valve cavity comprises a first cross-sectional width and the second valve cavity comprises a second cross-sectional width, wherein the second cross-sectional width is less than the first cross-sectional width such that a ridge is formed between the first and second valve cavities.

9. The needleless connector of claim 3, wherein, when the valve is compressed toward the base portion, the second end portion of the valve collapses before the first end portion of the valve.

10. The needleless connector of claim 3, wherein, when the second end portion of the valve collapses, the valve engages against the protrusion such that the first end portion of the valve moves in a direction that is transverse relative to the central longitudinal axis.

11. The needleless connector of claim 1, wherein the wall of the valve comprises first and second dimples, and wherein the proximal end of the protrusion is between the first dimple and the second dimple.

12. The needleless connector of claim 1, wherein an outer surface of the valve comprises a primary seal portion and a secondary seal portion, and wherein the primary seal portion is spaced apart from the secondary seal portion.

13. The needleless connector of claim 12, wherein the primary seal portion is configured to engage against the inner surface of the body portion to form a primary seal therebetween, and the secondary seal portion is configured to engage against the inner surface of the body portion to form a secondary seal therebetween.

14. The needleless connector of claim 13, wherein the inner surface of the body portion comprises a sealing edge between the first port and the base portion.

15. The needleless connector of claim 14, wherein the inner surface of the body portion comprises a fluid channel extending between the first port and the sealing edge.

16. A needleless connector comprising:
a housing comprising a central longitudinal axis, a body portion, and a base portion, the body portion comprising an inner surface forming a housing cavity, and a first port forming a first fluid passage to the housing cavity, the base portion comprising a top end section and a bottom end section, the top end section comprising a protrusion that extends from a central portion of the top end section in a direction away from the central longitudinal axis, and the bottom end section comprising a second port; and
a valve comprising a first end portion, a second end portion, and an inner surface forming a valve cavity, the valve having a closed configuration in which the first fluid passage is obstructed by the first end portion of the valve, and an open configuration in which the valve is compressed toward the base portion such that the first fluid passage is unobstructed,
wherein, when the valve moves from the closed configuration toward the open configuration, an inner surface of the valve extending partially around the central longitudinal axis engages against the protrusion such that the first end portion of the valve moves in a direction that is transverse relative to the central longitudinal axis.

17. The needleless connector of claim 16, wherein, when the valve moves from the closed configuration toward the open configuration, the inner surface of the valve engages against a proximal end of the protrusion.

18. The needleless connector of claim 16, wherein, when the valve moves from the closed configuration toward the open configuration, the first end portion begins to collapse after the second end portion begins to collapse.

19. The needleless connector of claim 16, wherein an outer surface of the valve comprises a primary seal portion and a secondary seal portion, and wherein, when the valve moves from the open configuration toward the closed configuration, the first end portion longitudinally expands such that the secondary seal portion and the primary seal portion move away from each other to form a vacuum between the outer surface of the valve and the inner surface of the body portion.

20. The needleless connector of claim 19, wherein the inner surface of the body portion comprises a fluid channel configured to permit a fluid to move between the secondary seal portion and the inner surface of the housing into an area between the secondary seal portion and the primary seal portion.

* * * * *